United States Patent [19]

Thiery et al.

[11] Patent Number: 4,994,114

[45] Date of Patent: * Feb. 19, 1991

[54] METHOD FOR SELECTING A POZZOLAN INTENDED TO BE INCORPORATED INTO A COMPOSITE MATERIAL COMPRISING CEMENT AND GLASS

[75] Inventors: Jacques Thiery, Villers-Les-Nancy; Pascal Soukatchoff, Lay Saint Christophe, both of France

[73] Assignee: Vetrotex Saint-Gobain, Chamberry, France

[ * ] Notice: The portion of the term of this patent subsequent to Dec. 27, 2005 has been disclaimed.

[21] Appl. No.: 376,477

[22] Filed: Jul. 6, 1989

[30] Foreign Application Priority Data

Jul. 13, 1988 [FR] France .................... 88 09567

[51] Int. Cl.$^5$ .................................. C04B 14/44
[52] U.S. Cl. .................................. 106/713; 106/701; 106/718
[58] Field of Search .................... 106/99, 85, 89, 713, 106/711, 819

[56] References Cited

U.S. PATENT DOCUMENTS

| | | | |
|---|---|---|---|
| 3,852,082 | 12/1974 | Majumdar | 106/99 |
| 4,640,715 | 3/1987 | Heitzmann et al. | 106/85 |
| 4,642,137 | 2/1987 | Heitzmann | 106/85 |
| 4,687,752 | 8/1987 | Peters | 501/121 |
| 4,793,861 | 12/1988 | Sohm | 106/99 |

FOREIGN PATENT DOCUMENTS

| | | |
|---|---|---|
| 0222339 | 5/1987 | European Pat. Off. . |
| 2309943 | 8/1974 | Fed. Rep. of Germany . |
| 1211265 | 3/1960 | France . |
| 2578778 | 9/1986 | France . |
| 847852 | 9/1960 | United Kingdom . |
| 1113205 | 5/1968 | United Kingdom . |
| 1314253 | 4/1973 | United Kingdom . |
| 1588938 | 4/1981 | United Kingdom . |
| 2148871 | 6/1985 | United Kingdom . |

OTHER PUBLICATIONS

Chemical Abstracts, vol. 102, No. 20, 171585(Y).
Benoit, M., "Determination de l'Activite Pouzzolanique d'Une Pouzzoalne par voie Chimique," 26 Bull. Liaison Labo. Routiers P. et Ch., D1–D5 (1967).
Largent, "Estimation de l'Activite Pouzzolanique,": 93 Bull. Liaison Labo. P. et Ch., 61 (1978).
British Standard Methods for Determining Properties of Glass Fibre Reinforced Cement Material, No. 6432 (1984).
Chemical Abstracts, vol. 98, No. 18 (Oct. 1982), Abstract No. 148630Z.

*Primary Examiner*—Karl Group
*Assistant Examiner*—Carol Bonner
*Attorney, Agent, or Firm*—Pennie & Edmonds

[57] ABSTRACT

According to the invention a pozzolan is selected which exhibits a capacity for fixing lime during the Chapelle test at 90° C. greater than 700 mg of CaO per gram of pozzolan, a capacity for fixing lime during the Chapelle test at 50° C. greater than 200 mg of CaO per gram of pozzolan and a ratio of the quantity of CaO fixed during the 50° C. Chapelle test to the specific surface area of the pozzolan which is greater than about 10 mg of CaO per square meter of pozzolan. The composite material obtained is used in construction to produce facade elements, for example, which have improved resistance to aging.

35 Claims, No Drawings

METHOD FOR SELECTING A POZZOLAN INTENDED TO BE INCORPORATED INTO A COMPOSITE MATERIAL COMPRISING CEMENT AND GLASS

FIELD OF THE INVENTION

This invention relates to a method for selecting a pozzolan intended to be incorporated with cement, glass fiber and, optionally other constituents to form a composite material. The invention is based on the selection of a pozzolan having several physiochemical properties which impart improved performance to composite materials containing such pozzolans.

This invention has particularly significant application, although not exclusively, in the area of mortars and concretes which are used in construction for producing slabs or panels which must be highly resistant to aging (facade coating or urban furniture, for example).

BACKGROUND ART

Reinforcing mineral binders of the cement or concrete type having glass fibers which are resistant to alkalines are known When such glass fibers are used, a problem of resistance and durability of the binder-fiber component arises. To eliminate this problem, one of the solutions contemplated is to add pozzolans to the cement matrix.

The term pozzolan is used here in the sense accepted by French Patent No. 2,149,998: they are silicates, of natural or synthetic origin, capable of reacting with lime and of being transformed into a hard and resistant material. They can be materials such as zeolites, illites or metakaolins for example.

Although the addition of pozzolan to cement reinforced with glass fibers is well known, all pozzolans do not confer on the final composite material the same mechanical properties. To select the pozzolans capable of conferring the best mechanical properties on the composite material, it is known to measure their specific surface area and their capacity for fixing lime. This is particularly the case with metakaolins.

The terms "metakaolin" and "metakaolinite" are used herein to mean an activated product of kaolinite, produced thermally or by any other means. The abbreviated formula for metakaolin can be written by using the standard symbols used by cement manufacturers, $AS_2$ ($A = Al_2O_3$ and $S = SiO_2$). It is obtained, for example, by heat treatment of kaolinite at temperatures ranging between 700° C. and 900° C. for several hours.

French Patent No. 2,601,356 describes cement-based products containing glass fibers resistant to alkalines and containing, per 100 parts by weight of cement, from about 10 parts to about 40 parts by weight of metakaolin. The metakaolin entering into the composition of this product must exhibit a minimum reactivity measured according to the Chapelle test at 90° C, as defined in the article by M. Benoit "Détermination de l'activite pouzzolanique d'une pozzolane par voie chimique" [Determining the pozzolanic activity of a pozzolane, chemically]—Bulletin de liaison des Laboratories Routiers des Ponts et Chaussees No. 26, 1967, pages D1 to D5, complemented by the article by R. Largent "Estimation de l'activite pouzzolanique - recherche d'un essai" [Estimate of pozzolan activity—investigation of a test]—Bulletin de liaison des Laboratoires des Ponts et Chaussees No. 93 of January/February 1978, ref. 2143. The metakaolins thus selected make it possible to achieve products which exhibit, on the average, good mechanical properties. However, measurements made on such products show that all these metakaolins do not exhibit the same advantages in the long term.

SUMMARY OF THE INVENTION

Following numerous laboratory tests performed by the inventors, it was discovered that the results of the 90° C Chapelle test and the selection of specific surface area characteristics do not make it possible to optimize the choice of the best metakaolin with certainty. It therefore became clear that even with the knowledge of these characteristics, it is necessary to measure the mechanical properties of the composite in order to refine the selection of the metakaolin.

To overcome this problem, the inventors researched a selection method, based on measuring a number of physiochemical characteristics, which meet the demands of actual practice better than those known previously. The present inventors performed tests on cement-based composites reinforced with alkali-resistant glass fibers consisting of between 20 and 30% metakaolin. Significantly, the present invention makes it possible to select a pozzolan (for example a metakaolin) in a repetitive, immediate and confident manner, thereby making it possible to obtain products exhibiting excellent resistance to breaking in both the short term and in the long term, while guaranteeing resistance, maintenance of ductility and, in general, good mechanical properties of the composite material in which the pozzolan has been incorporated. The invention therefore comprises a selection method which is sufficiently sure to substantially avoid performing extensive measurements on the composite, which are always long and costly in the long term.

The invention comprises a method for selecting a pozzolan, such as a metakaolin, intended to be incorporated into a composite material comprising cement and glass fibers, which includes the steps of measuring the specific surface area of the pozzolan and its capacity for fixing lime according to the Chapelle test at 90° C, its capacity for fixing lime according to the Chapelle test at 50° C, and calculating the ratio of the quantity of lime absorbed per gram of pozzolan during the 50° C Chapelle test to the specific surface area of said pozzolan, to deduce, from the different measurements and the ratios obtained, the capacity of the pozzolan for maintaining the mechanical properties of the composite material into which it is incorporated, after aging. The 50° C Chapelle test refers to a Chapelle test performed at a temperature on the order of 50° C for 16 hours, while the 90° C Chapelle test is conducted for 16 hours at 90° C.

The invention comprises selecting a pozzolan, such as a metakaolin, which exhibits a capacity for fixing lime during the 90° C Chapelle test of greater than 700 mg of CaO per gram of pozzolan; a capacity for fixing lime during the 50° C. Chapelle test of greater than 200 mg of CaO per gram of pozzolan; and a ratio of the quantity of lime absorbed per gram of pozzolan during the 50° C. Chapelle test to the specific surface area of the pozzolan which is greater than about 10 mg of CaO per square meter of pozzolan and preferably greater than 12 mg of CaO per square meter of pozzolan. The invention further comprises selecting a pozzolan which, in addition to meeting the aforementioned criteria, has a specific surface between about 10 m²/g and about 20 m²/g.

DETAILED DESCRIPTION OF THE PREFERRED EMBODIMENTS

The invention will be better understood by a review of the experimental results presented with comments below which were obtained from different metakaolins chosen as examples. The experimental composites were formed in the following manner:

The metakaolin was incorporated into the mixing water at the same time as the cement and the sand to form a mixture corresponding to the following proportions:

cement = 100 parts by weight
silica sand = 50 parts by weight
metakaolin between 10 and 40 parts by weight
water between 35 and 40 parts by weight
liquefier = from 1 to 3 parts by weight the liquefier being chosen from the additives commonly used by one skilled in the art, such as the sulfonates or the naphthalene sulfonates.

The composite was then produced by combining wet mortar whose composition is defined above with 3% to 6% by weight of alkali-resistant glass fibers in the composition.

In measuring the reactivity of the metakaolin during the 50° C Chapelle test and in linking this pozzolanic reactivity to the specific surface of the metakaolin grains, it became known to the inventors that the higher the ratio obtained, the more the detrimental results of aging of the material comprising glass and metakaolin, as selected, are limited, and therefore, the more the ductility is maintained. The reactivity of the metakaolin during the 50° C Chapelle test and its ratio to the specific surface area thus became known to the inventors to be complementary measurements and calculations which are indispensable and important in accurately measuring physiochemical characteristics of a metakaolin. The specific surface may be measured by any well known method, for example the BET method developed by Messrs. Brunauer, Emmet and Teller.

Following numerous tests performed on different test pieces comprising different metakaolins and whose physical characteristics were measured after aging, it came to light that utilizing a metakaolin exhibiting:

an $Ic_{90}$ reactivity during the 90° C Chapelle test greater than 700 mg of CaO per gram of metakaolin, an $Ic_{50}$ reactivity during the 50° C Chapelle test greater than 200 mg of CaO per gram of metakaolin, and an $Ic_{50}$ ratio on the BET specific surface of the metakaolin greater than about 10 mg and preferably greater than 12 mg of CaO per square meter of metakaolin, resulted in products exhibiting superior characteristics.

The inventors were also able to discover that, for a BET specific surface between approximately 10 $m^2/g$ and approximately 20 $m^2/g$ of metakaolin, even better results were obtained.

Several tests were performed, particularly from metakaolins whose specifications are given in Tables I and II located in the appendix, wherein metakaolin is symbolized by MK.

The composites comprising cement, metakaolin and alkali-resistant glass used for the tests and for which the results are found in Table III of the appendix, were performed according to the following procedure:

production of a wet mortar whose composition is the following:

CPA 55 = 100 parts by weight
silica sand (0–0.6 mm. grain size) = 50 parts by weight
metakaolin = 22.5 parts by weight
water = 40 to 46 parts by weight
liquefier = 1.5 to 3 parts by weight production by casting of composites from this mortar with a weight ratio on the order of 6% by weight of alkaliresistant glass, 24 hour curing under a polyurethane tarpaulin, then removal from the mold and curing for 27 days at 20.C at 98% relative humidity, then grinding and cutting from the test pieces, and aging in hot water at 50° C up to 84 days.

Then the samples are broken in saturated state (24 hours under water at 20° C) in 3 point bending (slenderness ratio of 150 to 1 mm/mn) on a universal machine of the type known by the name of INSTRON.

The metakaolins referred to in Table III are those defined in Tables I and II. The parameters LOP (Limit of Proportion); MOR (Modulus of Rupture) and $\epsilon$ or EPS (elongation at rupture) are defined in British Standard Methods For Determining Properties Of Glass Fiber Reinforced Cement Material, BS 6432, 1984.

All types of cements used for cements reinforced with glass fiber (GRC) can be used with the invention, particularly the standard type of Portland cement CPA.

The compositions of the alkali-resistant glass used are particularly compositions exhibiting more than 12% by weight of $ZrO_2$, and preferably more than 15%.

The selection of metakaolins No. 1 and 2 is within the scope of this invention, i.e., they exhibit characteristics meeting the specifications previously stated as a preferred embodiment, i.e.:

a BET specific surface between approximately 10 and 20 $m^2$ per gram,

Chapelle indices at 50° C and 90° C greater than 200 mg and 700 mg of CaO per gram of metakaolin respectively, and an $Ic_{50}$ ratio on BET specific surface area greater than 12 mg of CaO per square meter of metakaolin.

On the other hand, metakaolins 3, 4, 5 do not completely meet all four selection criteria:

metakaolin No. 3 does not meet any of the criteria, metakaolin No. 4 does not meet the criteria on the specific surface and the criterion on the reactivity ratio during the $Ic_{50}$ Chapelle test on the BET specific surface area of metakaolin, and metakaolin No. 5 does not meet the criterion relating to the Chapelle test at 90° C.

It can be observed that after 28 days of curing at 20° C and 98% relative humidity, the LOP, MOR and EPS ($\epsilon$) values are comparable for metakaolins No. 1, 2, 3 and 5. On the other hand, metakaolin No. 4 can lead to lower strengths considering its excessively high BET specific surface area.

After 84 days of aging under water at 50° C, there is observed on the other hand, a clear superiority of the composites produced with metakaolins No. 1 and 2, especially in regard to parameters EPS ($\epsilon$) and MOR. For these two metakaolins, the EPS ($\epsilon$) value at term is 0.7%, which makes it possible to assure maintenance of ductility and energies at rupture for composite material formed therewith containing alkali-resistant glass.

On the other hand, the composites produced with metakaolins No. 3, 4 and 5 exhibit drops in ductility ($\epsilon$) of at least 50%. This illucidates the advantages of the selection method of the invention. Without the new criteria of the invention, metakaolins No. 3, 4, 5 could have very likely been wrongly selected according to the prior art criteria. In particular, metakaolin No. 4 which exhibits good results according to prior art criteria is to be eliminated because of its excessively low Ic50/BET specific surface area ratio, metakaolin No. 3 for its insufficient capacity to fix lime, both at 50° C and at 90° C and metakaolin No. 5 for its likewise insufficient capacity to fix lime at 90° C in combination with specific surface that is slightly higher than preferable.

Thanks to this invention, it is therefore possible to select a pozzolan intended to be incorporated into a cementglass fibers composite, to confer on it sufficient ductility at long term, greater than 0.5%, as well as optimal strengths. Composites based on standard cement of the CPA type, comprising glass fiber and exhibiting such ductility, are not known by prior art. Such results for elongation are actually obtained after 20 days curing and 84 days aging, only with aluminous cements, exhibiting the disadvantage of undergoing an allotropic change with time and of necessarily being colored gray, and with very expensive supersulfated cements $C_4A_3S$ called "Chichibu" also exhibiting a necessarily colored appearance, i.e., not white. Those cements present disadvantages, such as strict conditions for curing (temperature and humidity), in contrast with the advantageous product resulting from the present invention. The composites produced from pozzolans selected according to this invention therefore exhibit minimal change over time.

The certainty of the method according to the invention makes it possible to select or eliminate a pozzolan, without it being necessary to perform additional, costly measurements on the composite. This certainty makes possible an absolutely remarkable saving in time and economy of means employed.

TABLE I

| | $SiO_2$ % | $Al_2O_3$ % | $Fe_2O_3$ % | $TiO_2$ % | CaO % | MgO % | $K_2O$ % | $Na_2O$ % | Loss on Ignition |
|---|---|---|---|---|---|---|---|---|---|
| MK n°1 | 59.65 | 36.08 | 1.93 | 0.25 | 0.29 | 0.15 | 0.41 | 0.02 | 1.37 |
| MK n°2 | 55.47 | 39.65 | 0.62 | 0.02 | 0.07 | 0.23 | 2.87 | 0.07 | 0.88 |
| MK n°3 | 54.72 | 42.18 | 0.57 | 0.01 | 0.05 | 0.20 | 1.46 | 0.05 | 0.41 |
| MK n°4 | 51.23 | 40.27 | 2.29 | 2.38 | 0.73 | 0.16 | 0.03 | 0.03 | 2.25 |
| MK n°5 | 51.48 | 43.26 | 1.17 | 1.37 | 0.32 | 0.05 | 0.5 | 0.04 | 1.39 |

MK = metakaolin

TABLE II

| | Surface BET $m^2/g$ | Chapelle Tests mg CaO/g Metakaolin | | Ic50/BET Mg CaO per $m^2$ of metakaolin |
|---|---|---|---|---|
| | | Ic50 | Ic90 | |
| MK n°1 | 17 | 260 | 770 | 15.3 |
| MK n°2 | 14.8 | 430 | 820 | 29 |
| MK n°3 | 8.3 | 100 | 570 | 12 |
| MK n°4 | 48.6 | 430 | 870 | 8.8 |
| MK n°5 | 24 | 240 | 630 | 10 |

TABLE III

| | LOP | MOR | ε | LOP | MOR | ε |
|---|---|---|---|---|---|---|
| | 28 days curing | | | 28 days curing and 28 days aging | | |
| 22.5% metakaolin n°1 | 12 | 28 | 0.94 | 13 | 29 | 0.80 |
| 22.5% metakaolin n°2 | 12 | 28 | 0.80 | 14 | 31 | 0.80 |
| 22.5% metakaolin n°3 | 14 | 27 | 0.9 | 15 | 31 | 0.60 |
| 22.5% metakaolin n°4 | 9 | 20 | 0.8 | 13 | 25 | 0.7 |
| 22.5% metakaolin n°5 | 11 | 29 | 0.97 | 13 | 21 | 0.4 |
| | 28 days curing and 56 days aging | | | 28 days curing and 84 days aging | | |
| 22.5% metakaolin n°1 | 12 | 28 | 0.70 | 13 | 29 | 0.70 |
| 22.5% metakaolin n°2 | 14 | 30 | 0.7 | 15 | 30 | 0.70 |
| 22.5% metakaolin n°3 | 15 | 31 | 0.60 | 16 | 28 | 0.40 |
| 22.5% metakaolin n°4 | 13 | 23 | 0.50 | 14 | 23 | 0.40 |
| 22.5% metakaolin n°5 | 13 | 20 | 0.25 | 14 | 17 | 0.15 |

We claim:

1. In a method for making a composite material comprising cement, the improvement which comprises adding to the cement a pozzolan which exhibits a capacity for fixing lime during the 90° C. Chapelle test greater than 700 mg of CaO per gram of pozzolan, a capacity for fixing lime during the 50° C. Chapelle test greater than 200 mg of CaO per gram of pozzolan, and a ratio of the quantity of lime absorbed per gram of pozzolan during the 50°C. Chapelle test to the specific surface area of the pozzolan which is greater than about 10 mg of CaO per square meter of pozzolan.

2. The method according to claim 1 wherein said pozzolan is a metakaolin.

3. The method according to claim 1 wherein the pozzolan is selected which also exhibits a specific surface between about 10 $m^2/g$ and about 20 $m^2/g$.

4. The method according to claim 3 wherein said pozzolan is a metakaolin.

5. The method according to claim 1 wherein the pozzolan is selected which exhibits a ratio of the quantity of lime absorbed per gram of pozzolan during the 50° C. Chapelle test to the specific surface of the pozzolan greater than 12 mg of CaO per square meter of pozzolan.

6. The method according to claim 5 wherein said pozzolan is a metakaoalin.

7. The method according to claim 5 wherein the pozzolan is selected which also exhibits a specific surface between about 10 $m^2/g$ and about 20 $m^2/g$.

8. The method according to claim 7 wherein said pozzolan is a metakaolin.

9. In a composite material comprising cement the improvement which comprises adding to cement a pozzolan which exhibits a capacity for fixing lime during the 90° C. Chapelle test greater than 700 mg of CaO per gram of pozzolan, a capacity for fixing lime during the 50° C. Chapelle test greater than 200 mg of CaO per gram of pozzolan, and a ratio of the quantity of lime absorbed per gram of pozzolan during the 50° C. Chapelle test to the specific surface area of the pozzolan which is greater than about 10 mg of CaO per square meter of pozzolan.

10. The composite material according to claim 9 wherein said pozzolan is a metakaolin.

11. The composite material according to claim 9 wherein the pozzolan exhibits a specific surface between about 10 $m^2g$ and about 20 $m^2/g$.

12. The composite material according to claim 9 wherein the pozzolan exhibits a ratio of the quantity of lime absorbed per gram of pozzolan during the 50° C. Chapelle test to the specific surface of the pozzolan greater than 12 mg of CaO per square meter of pozzolan.

13. In a method for making a composite material comprising cement, glass fibers and water, the improvement which comprises adding a pozzolan having a capacity for fixing lime during a Chapelle test at 90°C. greater than 700 mg of CaO per gram of pozzolan, a capacity for fixing lime during a Chapelle test at 50° C. greater than 200 mg of CaO per gram of pozzolan and a ratio of the quantity of lime absorbed per gram of pozzolan during the 50° C. Chapelle test to the specific surface area of the pozzolan which is greater than about 10 mg of CaO per square meter of pozzolan to form a mixture, and allowing said mixture to cure to a composite material having improved properties after aging under water.

14. A composite material produced by the method of claim 13.

15. In a composite material comprising cement and glass fibers, the improvement which comprises adding a pozzolan having a capacity for fixing lime during a Chapelle test at 90° C. greater than 700 mg of CaO per gram of pozzolan, a capacity for fixing lime during a Chapelle test at 50° C. greater than 200 mg of CaO per gram of pozzolan and a ratio of the quantity of lime absorbed per gram of pozzolan during the 50° C. Chapelle test to the specific surface area of the pozzolan which is greater than about 10 mg of CaO per square meter of pozzolan.

16. The composite material according to claim 15 wherein said pozzolan is a metakaolin.

17. The composite material according to claim 16 wherein the pozzolan exhibits a specific surface between about 10 $m^2/g$ and about 20 $m^2/g$.

18. The composite material according to claim 17 wherein the pozzolan exhibits a ratio between the quantity of lime absorbed per gram of pozzolan during the 50° C Chapelle test and the specific surface of the pozzolan greater than 12 mg of CaO per square meter of pozzolan.

19. The composite material according to claim 18 wherein between 10 and 40 parts by weight pozzolan is present per 100 parts by weight cement and the glass fibers are present in an amount of between about 3% to 6% of the total weight.

20. The method of claim 13 wherein the cement is Portland cement.

21. The method of claim 13 wherein the glass fibers are alkali-resistant.

22. The method of claim 21 wherein the glass fibers comprise more than 12 percent by weight of $ZrO_2$.

23. The method of claim 22 wherein the glass fibers comprises more than 15 percent by weight of $ZrO_2$.

24. The method of claim 13 wherein between 10 and 40 parts by weight of the pozzolan is added per 100 parts weight cement and the glass fibers are present in an amount of between about 3% to 6% of the total weight.

25. The method according to claim 13 wherein the pozzolan exhibits a specific surface between about 10 $m^2/g$ and about 20 $m^2/g$.

26. The method according to claim 13 wherein the pozzolan exhibits a ratio of the quantity of lime absorbed per gram of pozzolan during the 50° C. Chapelle test to the specific surface of said pozzolan greater than 12 mg of CaO per square meter of pozzolan.

27. The method according to claim 13 wherein the pozzolan is a metakaolin.

28. A method for making a composite material comprising cement, glass fibers and water which comprises adding a pozzolan having a capacity for fixing lime during a Chapelle test at 90° C. greater than 700 mg of CaO per gram of pozzolan, a capacity for fixing lime during a Chapelle test at 50° C. Greater than 200 mg of CaO per gram of pozzolan and a ratio of the quantity of lime absorbed per gram of pozzolan during the 50° C. Chapelle test to the specific surface area of the pozzolan which is greater than about 10 mg of CaO per square meter of pozzolan with cement and water to form a mixture, and then combining the mixture with glass fibers.

29. The method according to claim 28 wherein between 10 and 40 parts by weight of the pozzolan is added per 100 parts by weight cement and the glass fibers are present in an amount of between about 3% to 6% of the total weight.

30. The method according to claim 29 wherein between about 35 and 40 parts by weight of water is added per 100 parts by weight cement.

31. The method according to claim 29 wherein the glass fibers are alkali resistant.

32. The method according to claim 29 wherein the pozzolan exhibits a specific surface between about 10 $m^2/g$ and about 20 $m^2/g$.

33. The method according to claim 30 wherein the pozzolan exhibits a ratio of the quantity of lime absorbed per gram of pozzolan during the 50° C. Chapelle test to the specific surface of said pozzolan greater than 12 mg of CaO per square meter of pozzolan.

34. The method according to claim 32 wherein the glass fibers comprise more than 12 percent by weight $ZrO_2$.

35. The method according to claim 34 wherein the glass fibers comprise more than 15 percent by weight $ZrO_2$.

* * * * *

UNITED STATES PATENT AND TRADEMARK OFFICE
CERTIFICATE OF CORRECTION

PATENT NO. : 4,994,114

DATED : Feb. 19, 1991

INVENTOR(S) : Thiery et al

It is certified that error appears in the above-identified patent and that said Letters Patent is hereby corrected as shown below:

IN THE CLAIMS:

Claim 28, line 6, delete "Greater" and insert --greater-- therefor.

Claim 33, line 1, delete "30" and insert --29-- therefor.

Claim 34, line 1, delete "32" and insert --31-- therefor.

Signed and Sealed this

Seventh Day of May, 1991

Attest:

HARRY F. MANBECK, JR.

Attesting Officer

Commissioner of Patents and Trademarks